(12) United States Patent
Vogel (10) Patent No.: US 11,219,352 B2
(45) Date of Patent: Jan. 11, 2022

(54) ENDOSCOPE WITH OPTICS FOR CORRECTING ABERRATIONS CAUSED BY VIEWING WINDOW

(71) Applicant: KARL STORZ SE & CO. KG, Tuttlingen (DE)

(72) Inventor: Walter Vogel, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 112 days.

(21) Appl. No.: 16/544,647

(22) Filed: Aug. 19, 2019

(65) Prior Publication Data

US 2019/0365207 A1 Dec. 5, 2019

Related U.S. Application Data

(63) Continuation of application No. 14/491,472, filed on Sep. 19, 2014, now abandoned.

(30) Foreign Application Priority Data

Sep. 20, 2013 (DE) .......................... 102013110423.1

(51) Int. Cl.
*A61B 1/00* (2006.01)

(52) U.S. Cl.
CPC ...... *A61B 1/00096* (2013.01); *A61B 1/00165* (2013.01); *A61B 1/00183* (2013.01); *A61B 1/00195* (2013.01)

(58) Field of Classification Search
CPC . A61B 1/00183; A61B 1/002; A61B 1/00188; A61B 1/0019
See application file for complete search history.

(56) References Cited

U.S. PATENT DOCUMENTS

| | | | |
|---|---|---|---|
| 4,784,118 A | 11/1988 | Fantone | |
| 5,519,532 A | 5/1996 | Broome | |
| 5,523,181 A * | 6/1996 | Stonehart | H01M 8/1023 429/314 |
| 5,526,181 A | 6/1996 | Kunick | |
| 5,568,312 A | 10/1996 | Horton | |
| 5,576,882 A | 11/1996 | Kanamori | |
| 5,892,630 A | 4/1999 | Broome | |
| 6,088,157 A | 7/2000 | Mazurkewitz | |
| 6,530,882 B1 | 3/2003 | Farkas | |
| 6,615,072 B1 | 9/2003 | Izatt | |
| 2005/0018134 A1 * | 1/2005 | Noda | A61B 3/132 351/205 |

(Continued)

FOREIGN PATENT DOCUMENTS

| | | |
|---|---|---|
| DE | 1959719 | 5/1967 |
| DE | 102010050931 | 5/2012 |

(Continued)

*Primary Examiner* — Alexandra L Newton (74) *Attorney, Agent, or Firm* — Michael J Loi; David Noel Villalpando (57) ABSTRACT

An endoscope includes a window component made of a transparent material at the distal end of the endoscope, wherein the window component is not rotationally symmetric in relation to the direction of view, and an optical correction apparatus with a cylindrical lens for correcting the aberration of the window component. The correction apparatus may contain a second lens movable relative to the cylindrical lens.

7 Claims, 3 Drawing Sheets

(56) References Cited

U.S. PATENT DOCUMENTS

| | | |
|---|---|---|
| 2008/0249367 A1 | 10/2008 | Miyano |
| 2009/0147373 A1 | 6/2009 | Rolland |
| 2010/0324373 A1* | 12/2010 | Lei ..................... A61B 1/0676 |
| | | 600/176 |
| 2012/0265018 A1 | 10/2012 | Rehe |
| 2014/0275785 A1* | 9/2014 | Kesten ............... A61B 1/00183 |
| | | 600/117 |
| 2015/0359594 A1 | 12/2015 | Ben-Oren |

FOREIGN PATENT DOCUMENTS

| | | |
|---|---|---|
| EP | 20574268 | 4/2013 |
| WO | 201934 | 1/2002 |

* cited by examiner

ENDOSCOPE WITH OPTICS FOR CORRECTING ABERRATIONS CAUSED BY VIEWING WINDOW

CROSS-REFERENCE TO RELATED APPLICATIONS

This application is a continuation of U.S. patent application Ser. No. 14/491,472, filed 19 Sep. 2014, and entitled "Endoscope", which is hereby incorporated by reference, and which further claims priority to German patent application No. 102013110423.1, filed 20 Sep. 2013.

FIELD OF THE INVENTION

The present invention relates to an endoscope and, in particular to an endoscope with an adjustable direction of view and a non-spherical window component.

BACKGROUND OF THE INVENTION

At the distal end, an endoscope comprises a window component made of a transparent material, through which light emanating from an object to be observed can enter into the distal end of the endoscope. Light which has entered into the distal end of the endoscope through the window component can be imaged by means of an objective and converted into an electric signal by means of a camera or transmitted to the proximal end of the endoscope by means of a coherent bundle of optical fibers or by means of a relay lens system. Particularly in the case of endoscopes for medical applications, the window component hermetically seals the distal end of the endoscope in order to avoid the ingress of dirt, water vapor and other bothersome or destructively acting substances into the endoscope.

In the case of endoscopes with a fixed direction of view, i.e. with an unchanging angle between the direction of view and the longitudinal axis of the shaft, the window component is generally a plate with two plane and parallel surfaces, or at least with rotational symmetry in relation to the optical axis or to the direction of view. In the case of an endoscope with an adjustable direction of view, i.e. with a modifiable angle between the direction of view and the longitudinal axis of the shaft, the window component may have the form of a section of a circular cylinder barrel, wherein the cylinder axis 28 is parallel to the swivel axis 33 of the direction of view, orthogonal to the direction of view and orthogonal to the longitudinal axis of the shaft.

In the geometric sense meant here, a cylinder is a body which is delimited by two plane and parallel surfaces, which are also referred to as base and top surface, and by a lateral or cylinder surface. In the following, the plane and parallel base and top surfaces play no role and are, in particular, removed or modified by grinding or in any other way. The lateral or cylinder surface is formed by parallel straight lines, which connect mutually corresponding points on the edges of the plane surfaces. Thus, a cylinder is created by displacing a plane surface or curve along a straight line not lying in the plane. Base and top surface can be circular or have any other form. If the base surface and the top surface are circular, the cylinder is a circular cylinder. If the straight lines forming the lateral or cylinder surface are perpendicular to the plane surfaces, the cylinder is referred to as a right cylinder.

A cylinder axis of a cylinder refers here to any straight line which is parallel to the straight lines that form the lateral or cylinder surface. The cylinder axis specifies the direction in which the cylinder is translation invariant within certain limits. The cylinder axis of a circular right cylinder is the straight line on which the center points of base and top surface lie. The circular right cylinder is rotationally symmetric in relation to this axis of symmetry.

With increasing miniaturization of, also, endoscopes with an adjustable direction of view, the ratio between the wall thickness and the radius of curvature of the window component increases. As a result, the aberrations generated by the window component, in particular the astigmatism, increase, also on the optical axis. In order to avoid these imaging aberrations, use is made of a spherical window component. Protruding edges, which can simplify manufacture, in particular the joining of the spherical window component to the distal end of the barrel of the shaft, are often provided laterally of the spherical window component. These protruding edges can furthermore prevent a protrusion of the spherical window component and thus minimize the risk of damage or destruction. However, contaminants, which adversely affect the view and which may make cleaning of the endoscope more difficult, may be deposited in the resulting concave sections.

BRIEF SUMMARY OF THE INVENTION

An object of the present invention consists of developing an improved endoscope, in particular an improved endoscope with an adjustable direction of view.

This object is achieved by the subjects of the independent claims.

Developments are specified in the dependent claims.

An endoscope comprises a window component made of a transparent material at the distal end of the endoscope, wherein the window component is not rotationally symmetric in relation to the direction of view, and an optical correction apparatus for correcting the aberration of the non-spherical window component.

The endoscope is provided and embodied for medical, technical or other non-medical applications. The window component comprises a material which has a high transmission for light in the wavelength range visible to the human eye and/or for light in a different wavelength range, in which an object is intended to be observed by means of the endoscope. In particular, the window component is non-spherical. A window component is non-spherical if at least either the inner (proximal) or outer (distal) surface thereof is non-spherical or not in the shape of a sphere. A plane surface is a spherical surface with an infinite radius.

The optical correction apparatus is, in particular, provided and embodied for correcting an axial astigmatism of the window component. The optical correction apparatus may comprise one or more lenses or other optical elements. The optical correction apparatus can be embodied as a mechanically and/or optically independent unit, which only serves for correcting the aberration of the non-spherical window component. Alternatively, the optical correction apparatus can be partly or wholly integrated into another optical apparatus, for example into an objective, a rod lens or an eyepiece.

The optical correction apparatus for correcting the aberration enables, in particular, the use of a non-spherical window component which, inter alia, may have advantages over a spherical window component in respect of the mechanical robustness, the production complexity, the production costs and the assembly complexity. At the same time, the use of the optical correction apparatus enables optical properties and, in particular, an imaging quality which are at least comparable to those of a spherical window component.

In the case of an endoscope, as is described here, the direction of view, in particular, of the endoscope is adjustable.

An adjustability of the direction of view means, in particular, a changeability of the angle between the direction of view and the longitudinal axis of the shaft of the endoscope at the distal end of the latter. It may be desirable and advantageous, particularly in the case of an endoscope with an adjustable direction of view, to use a window component which is non-rotationally symmetric in relation to the direction of view and, in particular, non-spherical.

In the case of an endoscope, as is described here, the window component has, in particular, the form of a section of a circular cylinder barrel.

In particular, the window component essentially has the form of a rectangular section of a circular cylinder barrel, wherein two edge sections of the window component lying opposite one another respectively are straight and parallel to one another and two further edge sections of the window component lying opposite one another respectively have a circular arc shape and are parallel to one another. The inner and the outer surface of the window component each have the form of a section of a surface of a circular cylinder, wherein, in particular, the two circular cylinders have different radii and wherein, in particular, the axes of symmetry of the two circular cylinders coincide A window component in the form of a section of a circular cylinder barrel can be produced particularly cost-effectively. In particular, the window component is cut out of a cylindrical tube. In the case of an embodiment as a section of a circular cylinder barrel, a reflection-reducing coating and/or any other tempering of the surfaces of the window component can also be produced with particularly high quality and/or with comparatively little complexity, and therefore in a cost-effective manner. Furthermore, a window component in the form of a section of a circular cylinder barrel can be soldered or otherwise joined to the shaft of the endoscope in a particularly simple and/or precise manner. Furthermore, together with surrounding regions of the outer surface of the shaft of the endoscope, a window component in the form of a section of a circular cylinder barrel can form a particularly flat surface without gaps or other concave regions.

In the case of an endoscope, as is described here, the non-spherical window component and the optical correction apparatus together are optically equivalent to, in particular, a transparent spherical component. Expressed differently, a fictitious transparent spherical component is split or divided into two components which, taken together, are optically equivalent or substantially equivalent, namely into, firstly, the window component and, secondly, the optical correction apparatus. Here, both components are, in particular, cylindrical or substantially cylindrical in each case. The cylinder axes of both components are, in particular, parallel to one another. Alternatively, the cylinder axes of the two components may be orthogonal to one another.

In the case of an endoscope, as is described here, the correction apparatus comprises, in particular, a cylinder lens.

In particular, the window component is embodied as a section of a circular cylinder barrel and the cylinder lens is embodied as a converging cylinder lens, wherein the cylinder axis of the cylinder lens (the cylinder axis of a cylinder lens, as is known in the art, is generally referred to as the plano axis 61, as opposed to the power axis 60 of the lens) is parallel to the cylinder axis of the window component.

The cylinder lens can have both a convex and a concave embodiment. If the non-spherical window component has the form of a section of a circular cylinder barrel, the cylinder lens is, in particular, convex if the cylinder axis of the cylinder lens is parallel to the cylinder axis of the circular cylinder barrel and concave if the cylinder axis of the cylinder lens is orthogonal to the optical axis and orthogonal to the cylinder axis of the circular cylinder barrel.

The cylinder axis (piano axis) of a cylinder lens specifies the direction in relation to which both the light-entry surface and the light-emergence surface respectively are parallel. Expressed differently, both the light-entry surface and the light-emergence surface are respectively formed by a set of straight-line sections, which are parallel to the cylinder axis. Top and base surface of an ideal cylinder in the geometric sense play no role in a cylinder lens. In general, the top and base surfaces are removed and the cylinder lens is adapted to an in particular circular cross-section of adjacent lenses in a plane perpendicular to the propagation direction of the light and parallel to the cylinder axis of the cylinder lens.

A cylinder lens is convex if it is thicker in the center, or on the optical axis, than at the edge. In particular, the light-entry surface and the light-emergence surface of a convex cylinder lens are respectively convex. Alternatively, one of the two light-entry and emergence surfaces is convex and the other one is concave, wherein the curvature of the convex one is greater than that of the concave one.

A cylinder lens is concave if it is thinner in the center, or on the optical axis, than at the edge. In particular, the light-entry surface and the light-emergence surface of a concave cylinder lens are respectively concave. Alternatively, one of the two light-entry and emergence surfaces is convex and the other one is concave, wherein the curvature of the concave one is greater than that of the convex one.

In the case of an endoscope, as is described here, the correction apparatus is disposed, in particular, in the vicinity of the window component.

In particular, the correction apparatus is disposed distally of a rod lens system or any other relay lens system. The distal arrangement of the correction apparatus enables a transmission by means of the rod lens system or relay lens system of an image already corrected in respect of the aberration of the non-spherical window component.

An endoscope, as is described here, furthermore comprises, in particular, a swivelable optical apparatus for adjusting the direction of view of the endoscope, wherein the correction apparatus is disposed proximally of the swivelable optical apparatus.

The swivelable optical apparatus comprises, in particular, one or more reflecting surfaces, of which at least one can be swiveled about an axis orthogonal to the longitudinal axis of the shaft of the endoscope at the distal end thereof, and orthogonal to all adjustable directions of view. In particular, the swivelable optical apparatus comprises a swivelable dove prism or two deflection prisms, of which one is swivelable and which each provide deflection of, in particular, 90.degree. In particular, the correction apparatus is disposed immediately proximally of the swivelable dove prism or immediately proximally of the stationary one of two deflection prisms.

An endoscope, as is described here, furthermore comprises, in particular, an objective at the distal end of the endoscope, wherein the correction apparatus is integrated into the objective or disposed immediately distally or proximally of the objective.

In particular, the correction apparatus is disposed between the objective and the distal end of a rod lens system or any other relay lens system. This can allow a conventionally small distance between, firstly, the objective and, secondly, the non-spherical window component and a swivelable optical apparatus proximal of same.

An endoscope, as is described here, furthermore comprises, in particular, a relay lens system for transmitting an image from the distal end to the proximal end of the endoscope, wherein the correction apparatus is integrated into the relay lens system or disposed between two parts of the relay lens system.

The relay lens system is, in particular, a rod lens system made of a plurality of rod lenses. The correction apparatus is disposed, in particular, between two rod lenses. Alternatively, one rod lens is simultaneously embodied as correction apparatus. To this end, the rod lens has, in particular, an astigmatism or any other deviation from a perfect rotational symmetry in relation to the optical axis which is suitable for correcting the aberration of the non-spherical window component.

In the case of an endoscope, as is described here, the correction apparatus is, in particular, disposed on, or in the vicinity of, the proximal end of the endoscope.

An endoscope, as is described here, furthermore comprises, in particular, an eyepiece at the proximal end of the endoscope, wherein the correction apparatus is integrated into the eyepiece or disposed immediately distally or immediately proximally of the eyepiece.

An arrangement of the correction apparatus at, or in the vicinity of, the proximal end of the endoscope and, in particular, immediately distally or immediately proximally of the eyepiece, or an embodiment of the correction unit as part of the eyepiece, enables a correction of further aberrations by means of the correction apparatus when manufacturing the endoscope from distal to proximal. These further aberrations, which are correctable by the correction apparatus, may include errors which are caused by an imperfect or defective (e.g. tilted) assembly of the window component, of a swivelable optical apparatus, of an objective, of a relay lens system or of parts of a relay lens system. Disposing the correction apparatus at, or in the vicinity of, the proximal end of the endoscope and a correspondingly late assembly of the correction apparatus may increase the optical quality of the manufactured endoscope and reduce the proportion of faulty products or of rejects, and hence reduce the overall production costs.

In the case of an endoscope, as is described here, the correction apparatus has, in particular, an adjustable corrective effect in order to enable an adaptability of the corrective effect to the refractive index of a medium, in which the distal end of the endoscope is disposed.

Particularly in the case of medical applications, endoscopes are often used alternately in air, carbon dioxide or any other gas and in water, aqueous solutions or other transparent liquids. The dependence of the refractive effect of the outer surface of the window component on the refractive index of the surrounding medium can readily be compensated for in many cases by means of the apparatus provided for focusing. However, the refractive index of the surrounding medium also influences the aberration, in particular the astigmatism, of a non-spherical window component. Therefore, different aberrations need to be corrected in a medium with a refractive index of 1 (air or other gases) and in a medium with a refractive index of >1 (water or any other liquid). An adjustable corrective effect of the correction apparatus can enable use of the endoscope with a perfectly or substantially perfectly corrected aberration of the non-spherical window component in media with different refractive indices.

In the case of an endoscope, as is described here, the corrective effect of the correction apparatus can be switched, in particular, between a first predetermined corrective effect for the use of the distal end of the endoscope in air or any other gas and a second predetermined corrective effect for the use of the distal end of the endoscope in water or a liquid with a similar refractive index.

In particular, the non-spherical window component has two different values for the astigmatism in, firstly, air or any other gas and, secondly, in water or a liquid with a similar refractive index. The correction apparatus can be switched between two corrective effects provided for correcting respectively one of the two astigmatism values. In particular, the correction apparatus comprises at least one optical element, which is displaceable between two predetermined positions (parallel to the optical axis) or rotatable (about the optical axis). The two predetermined positions are defined, in particular, by mechanical stops or latching positions.

BRIEF DESCRIPTION OF THE SEVERAL VIEWS OF THE DRAWINGS

In the following text, embodiments are described in more detail on the basis of the attached figures. In detail.

DETAILED DESCRIPTION OF THE INVENTION

Figure 1:
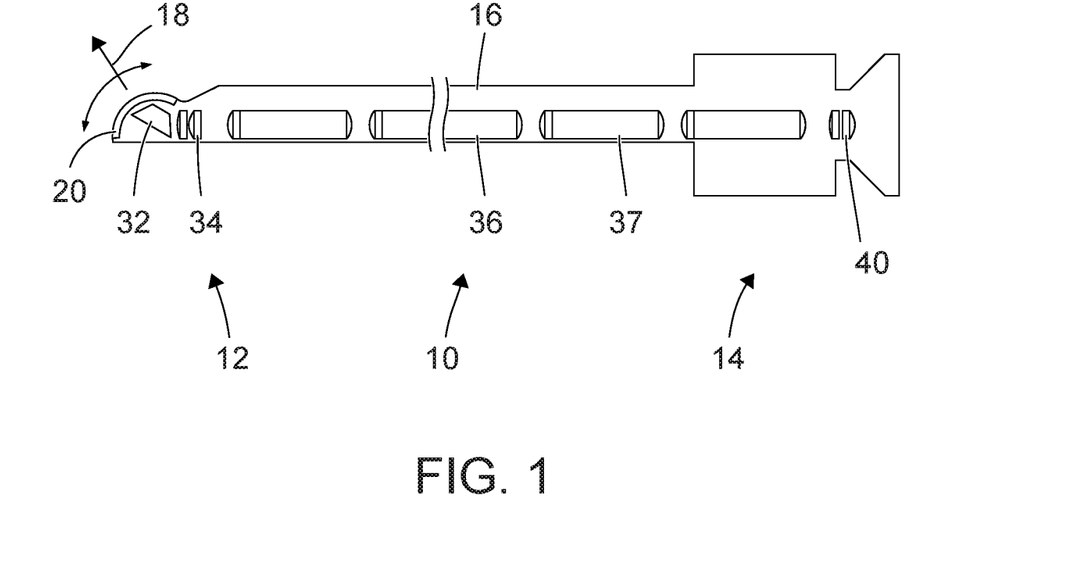
FIG. 1 shows a schematic illustration of an endoscope.

FIG. 1 shows a schematic illustration of an endoscope 10 comprising a distal end 12 and a proximal end 14. A straight and rigid shaft 16 extends from the distal end 12 to the proximal end 14 of the endoscope 10. The direction of view 18 of the endoscope 10 can be adjusted within an angular range indicated in FIG. 1 by a bent double-headed arrow.

The endoscope 10 and the features thereof described so far are substantially indicated by contours in FIG. 1. By contrast, the optical apparatuses described below are indicated in a side view. Depicted here in projection on the plane of the drawing are not only the external contours of the optical apparatuses, as become visible in the case of a section along a plane containing the optical axis, but also edges which arch out of the plane of the drawing, in particular with a circular arc shape. It is possible to identify, in particular, circular arc-shaped edges between arched light-entry surfaces or light-emergence surfaces on the one hand and cylindrical lateral surfaces on the other hand as straight lines orthogonal to the longitudinal axis of the endoscope 10 since these circular arc-shaped edges lie in planes orthogonal to the optical axis and therefore also orthogonal to the longitudinal axis of the endoscope 10 and to the plane of the drawing. Furthermore, the likewise circular arc-shaped edges of interfaces between elements cemented together can be identified as straight lines.

At the distal end 12, the endoscope 10 comprises a window component 20 made of a material which is transparent, in particular, to light within the wavelength range visible to the human eye or which has the highest possible transmission. The window component 20 has the form of a section of a circular cylinder barrel, wherein the cylinder axis 28 of the circular cylinder barrel is orthogonal to the optical axis of further optical apparatuses of the endoscope 10, orthogonal to the longitudinal axis of the shaft 16, orthogonal to the direction of view 18 of the endoscope and orthogonal to the plane of the drawing. The outer surface of the window component 20 is a light-entry surface; the inner surface of the window component 20 is a light-emergence surface for light which emanates from an object to be observed, lying approximately in the direction of view 18 of the endoscope 10, and which light enters into the endoscope 10 through the window component 20. The outer entry surface and the inner light-emergence surface of the window component 20 each have the form of a section of a surface of a circular cylinder, wherein the cylinder axes of both circular cylinders coincide such that the window component 20 has a constant wall thickness. The window component 20 is joined to the shaft 16 of the endoscope 10 by soldering or in any other way such that it hermetically seals an opening at the distal end 12 of the endoscope 10.

A swivel prism 32 is disposed directly proximally to, and downstream in the direction of light propagation of, the window component 20. The swivel prism 32 in particular has the form of a dove prism and can swivel about a swivel axis 33 (see FIG. 2 for an exemplar position of swivel axis 33) orthogonal to the plane of the drawing of FIG. 1 in order to set the direction of view 18.

An objective 34 made of one or more lenses or any other imaging apparatus for generating an intermediate image of an object observed by means of the endoscope 10 is disposed downstream of the swivel prism 32 in the direction of light propagation. A rod lens system made of a plurality of rod lenses 36, 37 or any other relay lens system for transmitting the intermediate image generated by the objective 34 to the distal end 14 of the endoscope 10 is disposed proximally and downstream of the objective 34 in the direction of light propagation in the shaft 16. An eyepiece 40 for generating a virtual image which can be registered by the human eye is disposed proximally and downstream of the rod lens system 36, 37 in the direction of light propagation. The eyepiece 40 may comprise a plurality of lenses and is simultaneously able to hermetically seal the endoscope 10 at the proximal end 14.

As a result of its non-spherical but rather circular cylinder barrel-shaped design, the window component 20 at the distal end 12 of the endoscope 10 generates imaging errors or aberrations which increase with increasing ratio of the wall thickness to the radius of curvature of the window component 20 and with increasing diameter of a light beam registered by means of the swivel prism, the objective 34, the rod lens system 36, 37 and the eyepiece 40. In particular, the window component 20 has an axial astigmatism. In order to correct the astigmatism, the objective 34, one or more of the rod lenses 36, 37 or the eyepiece 40 can be embodied as a correction apparatus, or one or more correction apparatuses, which are not depicted in FIG. 1, may be provided.

Figure 2:
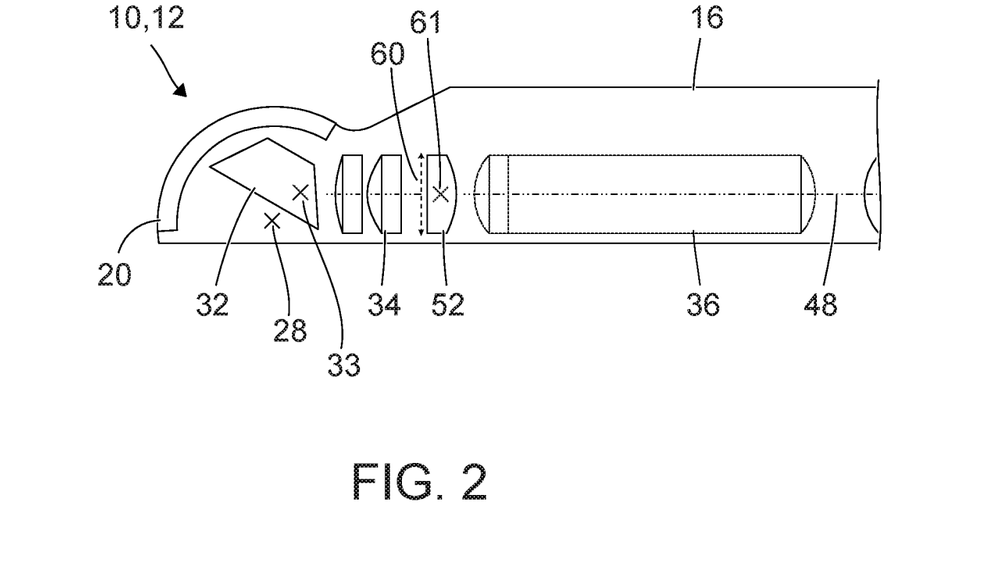
FIG. 2 shows a schematic illustration of part of the endoscope from FIG. 1.

FIG. 2 shows a schematic illustration of a distal end 12 of a further endoscope which, in terms of some features and properties, is similar to the endoscope depicted above on the basis of FIG. 1. The plane of the drawing and the type of representation in FIG. 2 correspond to those in FIG. 1. All that is described in the following are features and properties in terms of which the endoscope differs from the endoscope depicted above on the basis of FIG. 1.

At the distal end 12 of the endoscope, a correction apparatus in the form of a correction lens 52 is disposed immediately proximally of the objective 34 and immediately distally of the most distal rod lens 36, and therefore between the objective 34 and the most distal rod lens 36. The correction lens 52 is embodied as a cylinder lens, the cylinder (piano) axis 61 of which is orthogonal to the optical axis 48 of the objective 34 and of the rod lens 36, parallel to the cylinder axis 28 of the window component 20 and orthogonal to the plane of the drawing in FIG. 2. In particular, the correction lens 52 is embodied as a converging cylinder lens which, in the depicted projection, is thicker in the center than at the outside. In a projection (not shown) parallel to the optical axis 48 of the objective 34 and of the rod lenses 36, the correction lens 52 has, in particular, the same circular contour as the objective 34 and/or as the rod lens 36.

The correction lens 52 is provided and embodied for correcting the aberration of the non-spherical window component 20, in particular for correcting the astigmatism thereof. By way of example, disposing the correction lens 52 at the distal end 12 of the endoscope may be advantageous to the extent that an already corrected image is transmitted by the rod lenses 36. Furthermore, disposing the correction lens 52 at the distal end 12 enables use of a coherent bundle of optical fibers instead of the rod lenses 36, and therefore also the use of a flexible shaft 16.

Deviating from the illustration in FIG. 2, the correction lens 52 may be disposed distally of the objective 34 or between the swivel prism 32 and the objective 34 or between lenses of the objective 34. Furthermore, deviating from the illustration in FIG. 2, one or more lenses of the objective 34 may be embodied in such a way that they, instead of a correction lens 52, correct the aberration, in particular the astigmatism, of the window component 20.

Figure 3:
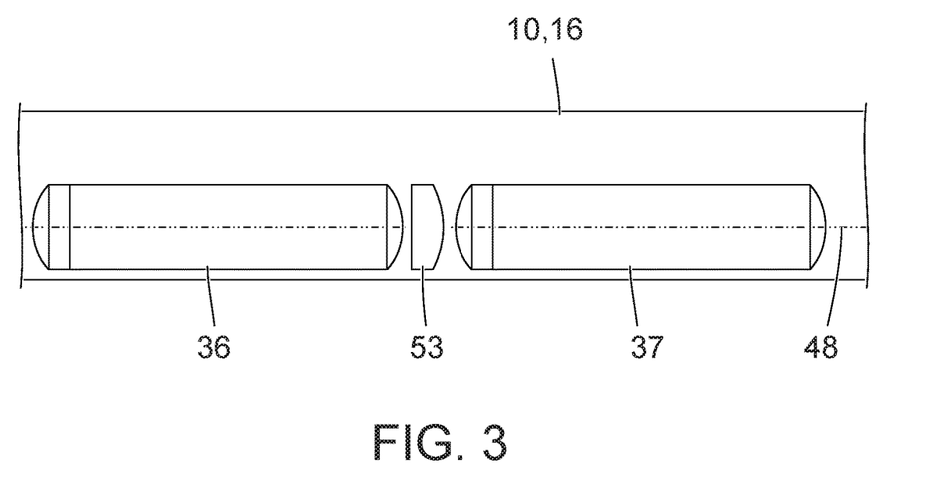
FIG. 3 shows a schematic illustration of part of a further endoscope.

FIG. 3 shows a schematic illustration of part of a shaft 16 of a further endoscope which, in terms of some features and properties, is similar to the endoscopes depicted above on the basis of FIGS. 1 and 2. The plane of the drawing and the type of representation correspond to those of FIGS. 1 and 2. All that is described in the following are features and properties in terms of which the endoscope 10 differs from the endoscopes depicted above on the basis of FIGS. 1 and 2.

In particular, the endoscope 10 differs from the endoscopes depicted above on the basis of FIGS. 1 and 2 in that a correction lens 53 is disposed between two rod lenses 36, 37 of a rod lens system. The correction lens 53 may have similar features and properties to the correction lens 52 of the endoscope 10 depicted above on the basis of FIG. 2.

Deviating from the illustration in FIG. 3, an effect of one or more rod lenses 36, 37 which corrects the aberration of the window component 20 may be provided instead of the correction lens 53 between the rod lenses 36, 37. In particular, one or more rod lenses 36, 37 may deviate from an ideal rotational symmetry with respect to the optical axis 48 and may have an astigmatism which corrects the astigmatism of the non-spherical window component 20 (cf. FIGS. 1, 2).

Figure 4:
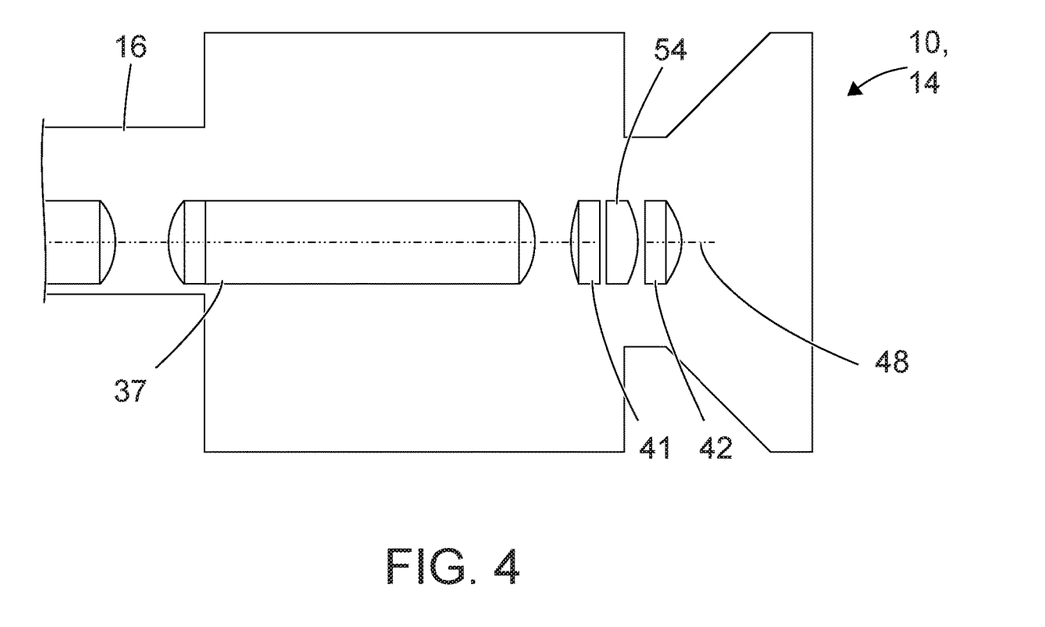
FIG. 4 shows a schematic illustration of part of a further endoscope.

FIG. 4 shows a schematic illustration of a proximal end 14 of a further endoscope 10 which, in terms of some features and properties, is similar to the endoscopes depicted above on the basis of FIGS. 1 to 3. The plane of the drawing and the type of representation correspond to those in FIGS. 1 to 3. All that is described in the following are features and properties in terms of which the endoscope 10 differs from the endoscopes depicted above on the basis of FIGS. 1 to 3.

At the proximal end 14, the endoscope 10 comprises a correction lens 54 for correcting the aberration of a non-spherical window component 20 (not depicted in FIG. 4) at the distal end 12 (cf. FIG. 1). The correction lens 54 is disposed, in particular, between lenses 41, 42 of an eyepiece. In particular, the correction lens 54 has features and properties which are similar to those of the correction lenses 52, 53 depicted above on the basis of FIGS. 2 and 3.

Deviating from the illustration in FIG. 4, the correction lens 54 may be disposed at the proximal end 14, either proximally of all lenses 41, 42 of the eyepiece or distally of all lenses 41, 42 of the eyepiece, and therefore between the most proximal rod lens 37 and the eyepiece 41, 42. Furthermore, as an alternative and deviating from the illustration in FIG. 4, an effect of one or more lenses 41, 42 of the eyepiece which corrects the aberration of the non-spherical window component may be provided instead of a correction lens 54. To this end, at least one of the lenses 41, 42, in particular, has a form which deviates from an ideal rotational symmetry in relation to the optical axis 48, deviating from the illustration in FIG. 4.

Disposing a correction lens 54 at the proximal end 14 of an endoscope 10 may be advantageous, particularly if the endoscope 10 is progressively assembled from the distal end 12 (cf. FIG. 1) to the proximal end 14. In this case, the correction lens 54 or a corresponding corrective effect of one or more lenses 41, 42 of the eyepiece may also, in addition to an aberration of a non-spherical window component 20, correct further imaging aberrations which, for example, are caused by an imprecise and no longer correctable arrangement or alignment of the window component 20, of the prism 32, of the objective 34 or of a rod lens 36, 37 (cf. FIG. 1) or by the non-ideal properties thereof.

Furthermore, a proximal arrangement of the correction lens 54 may enable a rotation of same when swiveling the direction of view 18 (cf. FIG. 1). This may be advantageous, in particular, if an arrangement of two deflection prisms or defection mirrors, of which one can be swiveled for adjusting the direction of view 18, is provided instead of a swivelable dove prism 32, as shown in FIG. 1 or 2. In this arrangement, which is similar to a periscope, swiveling the direction of view 18 is accompanied by a rotation of the image about the optical axis. A correction of an aberration generated by the window component 20 requires a rotation of the correction lens 54 corresponding to the rotation of the image. This rotation of the correction lens 54 can be realized particularly easily when disposing the correction lens 54 in the vicinity of the proximal end 14 of the endoscope 10.

Figure 5:
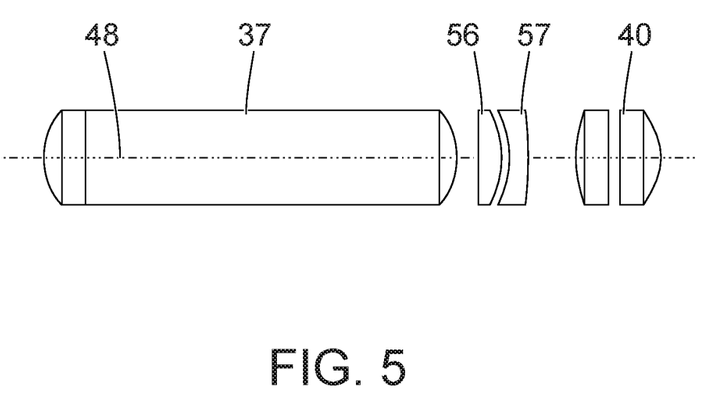
FIG. 5 shows a schematic illustration of part of a further endoscope.

FIG. 5 shows a schematic illustration of optical apparatuses of a further endoscope which, in terms of some features and properties, is similar to the endoscopes depicted above on the basis of FIGS. 1 to 4. The plane of the drawing and the type of representation in FIG. 5 correspond, or are similar, to those in FIGS. 1 to 4, wherein, deviating from the illustrations in FIGS. 1 to 4, only optical apparatuses, but not contours of the endoscope itself, are depicted. All that is described in the following are features and properties in terms of which the endoscope, in particular the optical apparatuses thereof, differs from the endoscope depicted above on the basis of FIG. 4.

In place of a single correction lens 54 (cf. FIG. 4), provision is made for two correction lenses 56, 57, of which at least one is displaceably disposed parallel to the optical axis 48 of the rod lenses 37 and of the eyepiece 40. The first correction lens 56 and the second correction lens 57 are embodied to have a combined corrective effect which depends on the spacing therebetween. In particular, the correction lenses 56, 57 are in each case cylindrical, wherein the cylinder axes are orthogonal to the optical axis 48 of the rod lens 37 and of the eyepiece 40, and orthogonal to the plane of the drawing in FIG. 5. In particular, one of the two correction lenses 56, 57 is diverging in the plane of the drawing and the other one is converging.

Figure 6:
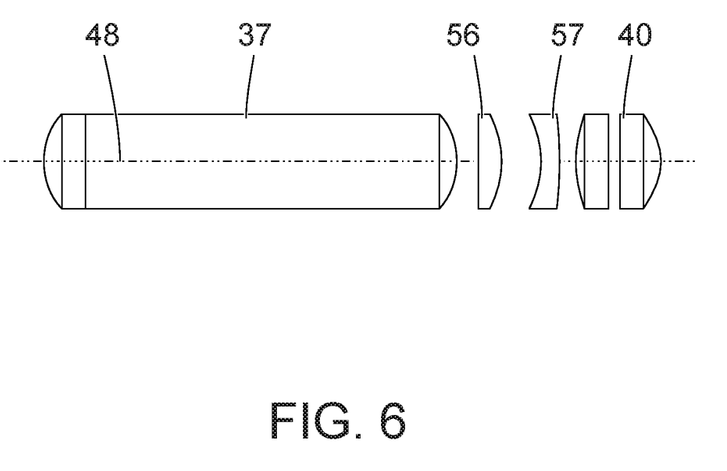
FIG. 6 shows a schematic illustration of part of a further endoscope.

FIG. 6 shows a further schematic illustration of the optical apparatuses 37, 40, 56, 57 of an endoscope, depicted above on the basis of FIG. 5. The illustration in FIG. 6 differs from the illustration in FIG. 5 in that, in particular, one of the two correction lenses 56, 57 is displaced relative to the other correction lens parallel to the optical axis 48 of the rod lens 37 and of the eyepiece 40. As a result, the correction lenses 56, 57 have different combined corrective effects in, firstly, the configuration depicted in FIG. 5 and, secondly, in the configuration depicted in FIG. 6. These different corrective effects can enable different aberrations to be corrected, which emerge from disposing the distal end 12 of the endoscope 10 (cf. FIG. 1) in media with different refractive indices.

The correction lens 57, which is displaceable parallel to the optical axis 48, is, within a hermetically sealed sleeve, mechanically coupled, in particular, to a permanent magnet (not depicted in FIGS. 5 and 6). With the aid of a further magnet outside of the hermetically sealed sleeve, the permanent magnet within the hermetically sealed sleeve and, thereby, the displaceable correction lens 57 can be moved in order to modify the corrective effect of the correction lenses 56, 57. Mechanical stops, likewise not depicted in FIGS. 5 and 6, may be provided in order to define two predetermined positions of the displaceable correction lens 57 and, accordingly, two predetermined correction values, for example, firstly, for air or a different gas and, secondly, for water or liquids with a similar refractive index.

REFERENCE SIGNS

10 Endoscope
12 Distal end of the endoscope 10
14 Proximal end of the endoscope 10
16 Shaft of the endoscope 10
18 Direction of view of the endoscope 10
20 Window component at the distal end 14 of the endoscope 10
28 Cylinder axis of the window component 20
32 Swivel prism at the distal end 14 of the endoscope 10
33 Swivel axis of the swivel prism
34 Objective
36 Rod lens in the shaft 16 of the endoscope 10
37 Rod lens in the shaft 16 of the endoscope 10
40 Eyepiece at the proximal end 12 of the endoscope 10A
41 First (distal) lens of the eyepiece 40
42 Second (proximal) lens of the eyepiece 40
48 Optical axis of the objective 34, of the rod lenses 36, 37 and of the eyepiece 40
52 Correction lens
53 Correction lens 52 as an element within the relay lens system
54 Correction lens 52 as an element of the eyepiece 40
56 Correction lens 52 as element of dual lens correction apparatus
57 Second correction lens of dual lens correction apparatus
60 Power axis of correction lens 52
61 Plano axis of first correction lens 52

The invention claimed is:

1. An endoscope comprising:
a non-spherical window component made of a transparent material at a distal end of the endoscope, wherein the non-spherical window component is not rotationally symmetric in relation to a direction of view of the endoscope, wherein the direction of view of the endoscope is variable, wherein each direction of view defines a field of view associated therewith, and wherein the range of view of the endoscope encompasses each field of view associated with all directions of view, and wherein the non-spherical window component has the form of a section of a circular cylinder barrel throughout the range of view of the endoscope; and
an optical correction apparatus for correcting the aberration of the non-spherical window component, wherein the correction apparatus comprises a cylinder lens and a second correction lens moveable relative to the cylinder lens, and wherein the cylinder lens is positionally fixed relative to the non-spherical window component.

2. The endoscope according to claim 1, further comprising a swivelable optical apparatus for adjusting the direction of view of the endoscope.

3. The endoscope according to claim 1, further comprising an eyepiece at the proximal end of the endoscope.

4. The endoscope according to claim 1, wherein the second correction lens is moveable relative to the cylinder lens in a direction parallel to an optical axis of the cylinder lens.

5. The endoscope of claim 1 wherein the second correction lens is a cylinder lens.

6. The endoscope according to claim 1, wherein the correction apparatus has a first corrective effect on an aberration of the non-spherical window component when the second correction lens is in a first position relative to the cylinder lens;
wherein the correction apparatus has a second corrective effect on the aberration of the non-spherical window component when the second correction lens is in a second position relative to the cylinder lens; and
wherein the first position is different than the second position, and the first corrective effect is different than the second corrective effect.

7. The endoscope according to claim 1, further comprising a relay lens system, comprising at least two optical elements separated by a first distance, for transmitting an image from the distal end to the proximal end of the endoscope, and wherein the correction apparatus is placed proximally of the relay lens system.

* * * * *